(12) United States Patent
Guo et al.

(10) Patent No.: US 10,455,849 B2
(45) Date of Patent: *Oct. 29, 2019

(54) METHOD FOR THE PREPARATION OF A PROTEIN PEPTIDE, A PROTEIN PEPTIDE AND USE THEREOF

(71) Applicant: INFINITUS (CHINA) COMPANY LTD., Jiang Men (CN)

(72) Inventors: Xiaolei Guo, Jiang Men (CN); Chung Wah Ma, Jiang Men (CN); Bin Shi, Jiang Men (CN); Ming Liang, Jiang Men (CN); Ting Zhang, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/140,925

(22) Filed: Apr. 28, 2016

(65) Prior Publication Data

US 2016/0316794 A1 Nov. 3, 2016

(30) Foreign Application Priority Data

Apr. 30, 2015 (CN) .......................... 2015 1 0222298

(51) Int. Cl.
| | |
|---|---|
| *A23J 1/04* | (2006.01) |
| *C07K 14/46* | (2006.01) |
| *C12P 21/06* | (2006.01) |
| *A23L 33/18* | (2016.01) |
| *A61K 38/00* | (2006.01) |

(52) U.S. Cl.
CPC ................. *A23J 1/04* (2013.01); *A23L 33/18* (2016.08); *C07K 14/461* (2013.01); *C12P 21/06* (2013.01); *A23V 2002/00* (2013.01); *A61K 38/00* (2013.01)

(58) Field of Classification Search
CPC .................................. A23J 1/04; A23L 33/18
See application file for complete search history.

(56) References Cited

FOREIGN PATENT DOCUMENTS

| | | | |
|---|---|---|---|
| CN | 102776262 A | * | 11/2012 |
| CN | 102808010 A | * | 12/2012 |

OTHER PUBLICATIONS

Motamedzadegan et al., "Optimization of enzymatic hydrolysis of yellowfin tuna *Thunnus albacares* viscera using Neutrase", Int Aquat Res (2010) 2: 173-181.*

* cited by examiner

*Primary Examiner* — Suzanne M Noakes
(74) *Attorney, Agent, or Firm* — Parker Highlander PLLC

(57) ABSTRACT

The present invention discloses a method for the preparation of a protein peptide, peptide powder prepared thereby, and use of the peptide powder in hypouricemic food products or health care products. The peptide powder is capable of inhibiting the activity of xanthine oxidase and effectively reducing uric acid. The method in an example of the present invention comprises: mincing the tuna, heating with steam or water to obtain a pretreated tuna, enzymolyzing the pretreated tuna, deactivating the enzyme, centrifuging, removing impurities to obtain a supernatant, concentrating, and drying to obtain the peptide powder of interest.

7 Claims, No Drawings

METHOD FOR THE PREPARATION OF A PROTEIN PEPTIDE, A PROTEIN PEPTIDE AND USE THEREOF

This application claims the benefit of priority to Chinese Patent Application No. 201510222298.5, filed Apr. 30, 2015. The entire content of the above-referenced disclosure is specifically incorporated herein by reference.

FIELD OF THE INVENTION

The present invention relates to the field of biochemistry, especially to a method for the preparation of a protein peptide, a protein peptide and use thereof.

BACKGROUND OF THE INVENTION

With the improvement of living standards and the change of diet structure of human being, the incidence of gout increases year by year, and the social concern thereon significantly increases. In recent years, the incidence of gout has shown a gradual increasing trend in both of the developed and developing countries, and the prevalence rate even reaches 20% in seriously affected areas. Drugs for the treatment of gout generally have serious discomfort and side effects. Therefore, in 2009, some experts on endocrine, metabolism, heart and cerebral vessels as well as scholars on nephropathy reached a consensus that conditioning by health care food would be a relatively reasonable method. Currently, the industry of healthy food all over the world enters a rapidly expanding period. In the recent two decades, due to the irrational diet structure, the sub-healthy population in our country expands, which also leads to the steadily rising trend of the medical expenses in our country in recent years.

Xanthine oxidase is a key enzyme involved in the development and progression of gout, and is also an important target for developing antigout drugs. Studies have shown that the inhibition of xanthine oxidase can effectively reduce the plasma uric acid level and thus can be used in the prevention and treatment of gout and hyperuricemia. Peptide is a functional fragment derived from a protein molecule, and its efficacy in assisting the treatment of gout have been occasionally reported in recent years, e.g., collagen and enzymatic hydrolysate thereof have significant efficacy on controlling uric acid (WO2008066070-A1, JP2008547008-X). Theoretically, bioactive peptides potentially have an important mechanism of action for improving hyperuricemia: regulating the key enzyme system for purine metabolism. The regulating effect of bioactive peptides on purine metabolism enzymes can be realized by the following routes: active peptides of protein are capable of chelating metal ions, while metal ions are activators for the catalytic activity of the key enzymes for purine metabolism, and thus chelation of related metal ions by peptides can inhibit activities of certain purine metabolism enzymes and reduce the generation of uric acid.

Currently commercially available uric acid-lowering food and health care products are mostly plant extracts, and the uric acid-lowering ingredients are indefinite and the uric acid-lowering efficacies are not significant.

SUMMARY OF THE INVENTION

The present invention provides a method for the preparation of a protein peptide, and a peptide powder prepared using the preparation method, and use of the peptide powder in uric acid-lowering food products or health care products.

The raw materials of the present invention come from tuna which is readily available. The prepared peptide powder shows significant uric acid-lowering efficacy and high inhibitory rate for xanthine oxidase, and can effectively improve gout syndrome as verified by animal experiments.

For this reason, the present invention provides a method for the preparation of a protein peptide, which can comprise:

(1) mincing the tuna, heating until cooked by water steam or water, to obtain a pretreated tuna;

(2) enzymolysing the pretreated tuna, deactivating the enzyme, centrifuging to obtain a supernatant; [11](3) concentrating the supernatant and drying to obtain the target peptide powder.

Preferably, the step of heating by water steam or water comprises heating at 80 to 100° C. for 5 to 30 min with water steam or water.

Preferably, the steps of enzymolysis and deactivating the enzyme comprise mixing the pretreated tuna with protease, allowing reaction at a temperature of 50 to 60° C. for 3.0 to 9.0 h; deactivating the enzyme at a temperature of 90 to 100° C. for 10 to 30 min after the completion of reaction.

Preferably, the protease used for enzymolysis consists of one or more of acid protease, papain, pepsin, trypsin, proteolytic enzyme, NEUTRASE® (*Bacillus amyloliquefaciens* protease), FLAVOURZYME® (*Aspergillus oryzae* protease) or ALCALASE® (*Bacillus lichenformis* protease), and the protease is used in an amount of 0.2% to 3.2% by weight of the pretreated tuna.

Preferably, the step of removing impurities in the supernatant comprises:

(1) adding activated charcoal to the supernatant in an amount of 0.3% to 2.5% by weight of the supernatant;

(2) stirring at 50 to 90° C. for 0.5 to 2.0 h;

(3) removing the activated charcoal by filtration.

Preferably, the step of concentrating is conducted to achieve a solids of 30% to 45% with a three-effect concentrator under a vacuum condition of 0.03 to 0.08 MPa at 60 to 80° C.

The tuna of the present invention is one or more of skipjack tuna, bluefin tuna, albacore tuna, and yellowfin tuna.

The present invention further provides a protein peptide prepared according to the above-mentioned preparation method, characterized in that the molecular weight of no less than 70% by weight of the protein peptide is less than 5000 Da.

The present invention further provides the use of a protein peptide prepared according to the above-mentioned preparation method in uric acid-lowering food and health care products.

In an example of the present invention, after the tuna is minced and a deodorization agent is added, food grade water in an amount of 1 to 10 times by weight of the tuna is added or water steam is used to heat at 80 to 100° C. for 5 to 10 min, and then the mixture is cooled down; acid protease, papain, pepsin, trypsin, proteolytic enzyme, NEUTRASE® (*Bacillus amyloliquefaciens* protease), FLAVOURZYME® (*Aspergillus oryzae* protease) or ALCALASE® (*Bacillus lichenformis* protease) according to the weight of the tuna (the added enzyme amount is 0.2% to 3.2%) are added, and the reaction is allowed under vibration in a 55° C. water bath for 3.0 to 8.0 h; after the reaction is completed, the hydrolysate is kept in boiling water for 10 to 20 min to deactivate the enzyme, and then centrifuged to obtain a supernatant; impurities is removed by activated charcoal, and the protein peptide is separated by ion-exchange resin as follows: adding 0.3% to 2.5% of activated charcoal to the supernantant by weight for rough filtration, stirring at 50 to 90° C. for 0.5 to 2.0 h; filtering the liquid material through a microfiltration device to remove the activated charcoal; using DEAE-52 cellulose anion-exchange column chromatography with 0.1 mol/L sodium chloride solution as eluent to carry out separation, and collecting the eluate. The eluate is concentrated with a three-effect concentrator to achieve a solids of 30% to 45% at a vacuum condition of 0.03 to 0.08 MPa at 60 to 80° C., and then spray-dried to obtain the peptide powder of interest. By monitoring with MALDI-TOF-MS mass spectrometry, all of the main effective peptide components have a molecular weight of less than 5000 Da.

The pretreated tuna is degraded into a protein peptide with a protease. The active protein peptide obtained is capable of chelating metal ions, while metal ions are activators for the catalytic reaction of xanthine oxidase which is the key enzyme in purine metabolism, and thus the chelation of metal ions by peptides can inhibit the activity of xanthine oxidase, reducing the generation of uric acid, lowering the plasma uric acid level, and thereby effectively preventing and treating gout and hyperuricemia.

DETAILED EMBODIMENTS

The examples of the present invention provide a method for the preparation of a protein peptide and a peptide powder prepared according to the method for improving gout syndrome.

In the method for the preparation of a protein peptide according to the present invention, the tuna is minced and heated at 80 to 100° C. with steam or water for 5 to 30 min to obtain pretreated tuna; the pretreated tuna is mixed with a protease at a reaction temperature of 50 to 60° C. for 3.0 to 9.0 h; after completion of the reaction, the enzyme is deactivated at a temperature of 90 to 100° C. for 10-30 min. The protease used is one or more of acid protease, papain, pepsin, trypsin, proteolytic enzyme, NEUTRASE® (*Bacillus amyloliquefaciens* protease), FLAVOURZYME® (*Aspergillus oryzae* protease) or ALCALASE® (*Bacillus lichenformis* protease), and the protease is used in an amount of 0.2% to 3.2% by weight of the pretreated tuna.

After the enzyme is deactivated, a supernatant is obtained through centrifugation, to which activated charcoal is added in an amount of 0.3% to 2.5% by weight of the supernatant. The resultant mixture is stirred at a temperature of 50 to 90° C. for 0.5 to 2.0 h, filtered to remove the activated charcoal, concentrated to achieve a solids of 30% to 45% with a three-effect concentrator under a vacuum condition of 0.03 to 0.08 MPa at 60 to 80° C. The peptide powder of interest is obtained after drying.

In practical application, the peptide powder of interest can be combined with Chinese herbal medicine such as Smilacis Glabrae Rhizoma, Cichorii Herba, Plantaginis Herba, Coicis Semen, etc. to prepare a health care food product or health care product having uric acid-lowering function.

In order to allow those skilled in the art to better understand the technical solution of the present invention, the present invention is further illustrated in detail through the following specific examples.

Example 1

The bluefin tuna, after the head and viscera of which being removed, were cleaned completely, and minced by a meat mincer to obtain 500 kg of minced meat of bluefin tuna. 1000 kg of water was added, and the resultant mixture was heated under stirring at 90° C. for 25 min to obtain a meat slurry of bluefin tuna, after that the temperature was lowered to 55° C. 13 kg of neutrase was added to the meat slurry of bluefin tuna, and the hydrolysis reaction was allowed to occur for 6 hours at a temperature kept at 55° C. The mixture was then heated at 90° C. for 20 min to deactivate the enzyme, and finally centrifuged. The obtained supernatant was the crude enzymatic hydrolysate of tuna, to which 5 kg of activated charcoal was added. The mixture was stirred for 0.8 hour at a temperature kept at 50° C., filtered through a 0.5 μm filter paper, and the obtained filtrate was the refined enzymatic hydrolysate of tuna, which was concentrated under vacuum to achieve a solids content of 30% and then spray-dried to obtain tuna extract 1.

The therapeutic effects of the tuna extract 1 on hyperuricemia rats induced by potassium oxonate are shown in Tables 1, 2, and 3.

The active protein peptide prepared according to the example of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia.

Example 2

(1) The bluefin tuna, after the head and viscera of which being removed, were cleaned completely, and minced by a meat mincer to obtain 500 kg of minced meat of yellowfin tuna. 500 kg of water was added, and the resultant mixture was heated under stirring at 80° C. for 30 min to obtain a meat slurry of yellowfin tuna, after that the temperature was lowered to 50° C.

(2) 3 kg of neutrase, 5 kg of flavourzyme and 3 kg proteolytic enzyme were added to the meat slurry of yellowfin tuna, and the hydrolysis reaction was allowed to occur for 8 hours at a temperature kept at 50° C. The mixture was then heated at 90° C. for 30 min to deactivate the enzymes, and finally centrifuged. The obtained supernatant was the crude enzymatic hydrolysate of tuna.

(3) 5 kg of activated charcoal was added to the crude enzymatic hydrolysate of tuna. The mixture was stirred for 0.5 hour at a temperature kept at 50° C., filtered through a 0.5 μm filter paper, and the obtained filtrate was the refined enzymatic hydrolysate of tuna.

(4) The refined enzymatic hydrolysate of tuna was concentrated under vacuum to achieve a solids of more than 30% and then spray-dried to obtain tuna extract 2.

The therapeutic effects of the tuna extract 2 on hyperuricemia rats induced by potassium oxonate are shown in Tables 1, 2, and 3.

The active protein peptide prepared according to the example of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia.

Example 3

(1) The skipjack tuna, after the head and viscera of which being removed, were cleaned completely, and minced by a meat mincer to obtain 250 kg of minced meat of skipjack tuna. The tuna, after the head and viscera of which being removed, were cleaned completely, and minced by a meat mincer to obtain 250 kg of minced meat of albacore tuna. The minced meat of the two kinds of fish was combined. 1500 kg of water was added, and the resultant mixture was heated under stirring at 100° C. for 10 min to obtain a meat slurry of skipjack tuna, after that the temperature was lowered to 50° C.

(2) 3 kg of acid protease, 3.5 kg of flavourzyme, 1 kg of papain, 1 kg of neutrase, 2 kg of Alcalase and 2 kg of trypsin were added to the meat slurry of skipjack tuna, and hydrolysis reaction was allowed to occur for 9 hours at a temperature kept at 50° C. The mixture was then heated at 95° C. for 15 min to deactivate the enzymes, and finally centrifuged. The obtained supernatant was the crude enzymatic hydrolysate of skipjack tuna.

(3) Activated charcoal was added to the crude enzymatic hydrolysate of skipjack tuna in an amount of 0.8% by weight. The mixture was stirred for 1.0 hour at a temperature kept at 50° C., filtered through a 0.5 µm filter paper, and the obtained filtrate was the refined enzymatic hydrolysate of skipjack tuna.

(4) The refined enzymatic hydrolysate of skipjack tuna was concentrated under vacuum to achieve a solids of 30% and then spray-dried to obtain tuna extract 3.

The therapeutic effects of the tuna extract 3 on hyperuricemia rats induced by potassium oxonate are shown in Tables 1, 2, and 3.

The active protein peptide prepared according to the example of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia.

Example 4

(1) The albacore tuna, after the head and viscera of which being removed, were cleaned completely, and minced by a meat mincer to obtain 500 kg of minced meat of albacore tuna. 1500 kg of water was added, and the resultant mixture was heated under stirring at 100° C. for 10 min to obtain a meat slurry of albacore tuna, after that the temperature was lowered to 50° C.

(2) 4 kg of acid protease, 4 kg of FLAVOURZYME® (*Aspergillus oryzae* protease) and 8 kg of papain were added to the meat slurry of albacore tuna, and hydrolysis reaction was allowed to occur for 9 hours at a temperature kept at 50° C. The mixture was then heated at 95° C. for 15 min to deactivate the enzymes, and finally centrifuged. The obtained supernatant was the crude enzymatic hydrolysate of albacore tuna.

(3) 50 kg of activated charcoal was added to the crude enzymatic hydrolysate of albacore tuna. The mixture was stirred for 1.0 hour at a temperature kept at 70° C., filtered through a 0.5 µm filter paper, and the obtained filtrate was the refined enzymatic hydrolysate of albacore tuna.

(4) The refined enzymatic hydrolysate of albacore tuna was concentrated under vacuum to achieve a solids of 35% and then spray-dried to obtain tuna extract.

The active protein peptide prepared according to the example of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia.

Example 5

(1) The albacore tuna, after the head and viscera of which being removed, were cleaned completely, and minced by a meat mincer to obtain 500 kg of minced meat of albacore tuna. 500 kg of water was added, and the resultant mixture was heated under stirring at 100° C. for 15 min to obtain a meat slurry of albacore tuna, after that the temperature was lowered to 50° C.

(2) 4 kg of acid protease and 4 kg of FLAVOURZYME® (*Aspergillus oryzae* protease) were added to the meat slurry of albacore tuna, and hydrolysis reaction was allowed to occur for 9 hours at a temperature kept at 55° C. The mixture was then heated at 95° C. for 15 min to deactivate the enzymes, and finally centrifuged. The obtained supernatant was the crude enzymatic hydrolysate of albacore tuna.

(3) 15 kg of activated charcoal was added to the crude enzymatic hydrolysate of albacore tuna. The mixture was stirred for 1.0 hour at a temperature kept at 80° C., filtered through a 0.5 µm filter paper, and the obtained filtrate was the refined enzymatic hydrolysate of tuna.

(4) The refined enzymatic hydrolysate of skipjack tuna was concentrated under vacuum to achieve a solids of 40% and then spray-dried to obtain tuna extract.

The active protein peptide prepared according to the example of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia.

Example 6

(1) The yellowfin tuna, after the head and viscera of which being removed, were cleaned completely, and minced by a meat mincer to obtain 500 kg of minced meat of yellowfin tuna. 500 kg of water was added, and the resultant mixture was heated under stirring at 90° C. for 25 min to obtain a meat slurry of yellowfin tuna, after that the temperature was lowered to 60° C.

(2) 2 kg of FLAVOURZYME® (*Aspergillus oryzae* protease) was added to the meat slurry of yellowfin tuna, and the hydrolysis reaction was allowed to occur for 9 hours at a temperature kept at 60° C. The mixture was then heated at 90° C. for 20 min to deactivate the enzymes, and finally centrifuged. The obtained supernatant was the crude enzymatic hydrolysate of tuna.

(3) 10 kg of activated charcoal was added to the crude enzymatic hydrolysate of tuna. The mixture was stirred for 1.5 hour at a temperature kept at 60° C., filtered through a 0.5 µm filter paper, and the obtained filtrate was the refined enzymatic hydrolysate of tuna.

(4) The refined enzymatic hydrolysate of tuna was concentrated under vacuum to achieve a solids of more than 45% and then spray-dried to obtain tuna extract.

The active protein peptide prepared according to the example of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia.

Comparative Example 1

(1) A: The Pacific saury, after the head and viscera of which being removed, were cleaned completely, and minced by a meat mincer to obtain 500 kg of minced meat of Pacific saury, 1000 kg of water was added, and the resultant mixture was heated under stirring at 80° C. for 30 min to obtain a meat slurry of Pacific saury, after that the temperature was lowered to 50° C.

B: The golden thread, after the head and viscera of which being removed, were cleaned completely, and minced by a meat mincer to obtain 500 kg of minced meat of golden thread, 1000 kg of water was added, and the resultant mixture was heated under stirring at 80° C. for 30 min to obtain a meat slurry of golden thread, after that the temperature was lowered to 50° C.

C: The Spanish mackeral, after the head and viscera of which being removed, were cleaned completely, and minced by a meat mincer to obtain 500 kg of minced meat of Spanish mackerel, 1000 kg of water was added, and the resultant mixture was heated under stirring at 80° C. for 30 min to obtain a meat slurry of Spanish mackerel, after that the temperature was lowered to 50° C.

(2) 6 kg of neutrase and 10 kg of FLAVOURZYME® (*Aspergillus oryzae* protease) were added to the meat slurry of the three kinds of fish meat slurry respectively, and hydrolysis reaction was allowed to occur for 8 hours at a temperature kept at 50° C. The mixtures were then heated at 95° C. for 15 min to deactivate the enzymes, and finally centrifuged. The obtained supernatants were crude enzymatic hydrolysate of the above three kinds of fish respectively.

(3) Activated charcoal was added to the crude enzymatic hydrolysate of the three kinds of fish in an amount of 0.5% by weight. The mixtures were stirred for 1.0 hour at a temperature kept at 50° C., filtered through a 0.5 µm filter paper, and the obtained filtrates were the refined enzymatic hydrolysate of the fish.

(4) The refined enzymatic hydrolysate of the three kinds of fish was respectively concentrated under vacuum to a solids of more than 30%, and then spray-dried to obtain Pacific saury extract, golden thread extract, and Spanish mackerel extract, respectively.

The therapeutic effects of the Pacific saury extract, golden thread extract and Spanish mackerel extract on hyperuricemia rats induced by potassium oxonate are shown in Tables 1, 2, and 3.

Comparative Example 2

(1) The bluefin tuna, after the head and viscera of which being removed, were cleaned completely, and minced by a meat mincer to obtain 500 kg of minced meat of bluefin tuna. 500 kg of water was added, and the resultant mixture was heated under stirring at 85° C. for 25 min to obtain a meat slurry of bluefin tuna, after that the temperature was lowered to 45° C.

(2) A: The pH of the meat slurry of bluefin tuna was adjusted to 8.0. 7.5 kg of ALCALASE® (*Bacillus lichenformis* protease) and 12.5 kg of FLAVOURZYME® (*Aspergillus oryzae* protease) were added, and the hydrolysis reaction was allowed to occur for 9 hours at a temperature kept at 45° C. The mixture was then heated at 95 to 100° C. for 15 to 30 min to deactivate the enzymes, and finally centrifuged. The obtained supernatant was enzymatic hydrolysate of tuna A.

B: The pH of the meat slurry of bluefin tuna was adjusted to 4.5. 7.5 kg of acid protease and 12.5 kg of FLAVOURZYME® (*Aspergillus oryzae* protease) were added, and hydrolysis reaction was allowed to occur for 9 hours at a temperature kept at 45° C. The mixture was then heated at 95 to 100° C. for 15 to 30 min to deactivate the enzymes, and finally centrifuged. The obtained supernatant was enzymatic hydrolysate of tuna B.

(3) 8 kg of activated charcoal was added to the enzymatic hydrolysate of tuna. The mixtures were stirred for 1.0 hour at a temperature kept at 50° C., filtered through a 0.5 µm filter paper, and the obtained filtrates were the extract solutions of tuna.

(4) The extract solutions of tuna were concentrated under vacuum and then spray-dried to obtain the extract of tuna of control groups A and B, respectively.

The therapeutic effects of the extract of tuna of control groups A and B on hyperuricemia rats induced by potassium oxonate are shown in Tables 1, 2, and 3.

180 SD rats (SPF grade, male, 200±20 (g)) were provided by Laboratory Animals Centre, Guangzhou University of Chinese Medicine (License Number: SCXK(Yue)2013-0020). Reagents: allopurinol tablets (Guangdong P.D. Pharmaceutical Co., Ltd., Production batch No. 20130302); potassium oxonate (Shandong Zhongke Taidou Chemical Co., Ltd., Batch No. 120901); sodium carboxymethyl cellulose (Shanghai Celluloid Factory, Product Standard No. GB2760); uric acid assay kit (NanJing Jiancheng Bioengineering Institute, Production batch No. 20130529).

Animal grouping and modeling: 165 normal healthy SD male rats were obtained and randomly divided into normal control group (15 rats) and model group (150 rats). The rats in model group were intragastricly administered with potassium oxonate (2 g·kg$^{-1}$) daily within 7 days, then anaesthetized with 3% pentobarbitol sodium (i.p., 30 mg·kg$^{-1}$), and the blood (0.5 ml) was collected from conjunctiva, centrifuged at 4° C., 3000 rpm for 15 min, and the supernatant sera was taken for determining the content of uric acid. The rats in normal control group were intragastricly administered with equal volume of solvent. Those rats having a uric acid content of greater than 110 µmol·L$^{-1}$ were determined to be successful models. The successful modeled rats were randomly divided into model control group (equal volume of solvent), drug peptide testing groups of tuna extract 1 (200 mg·kg$^{-1}$), tuna extract 2 (200 mg·kg$^{-1}$), tuna extract 3 (200 mg·kg$^{-1}$), Pacific saury extract (200 mg·kg$^{-1}$), golden thread extract (200 mg·kg$^{-1}$) and Spanish mackerel extract (200 mg·kg$^{-1}$), tuna extract control group A (200 mg·kg$^{-1}$), tuna extract control group B (200 mg·kg$^{-1}$), and allopurinol group (50 mg·kg$^{-1}$). Each group comprised 15 rats, which were intragastricly administered with a volume of 10 ml/kg. The rats in model group were administered with equal volume of distilled water. On 10th and 20th day after treatment with the above-described peptide samples, 50 min after the last administration, the rats were anaesthetized with 3% pentobarbitol sodium (i.p., 30 mg·kg$^{-1}$), and the blood (0.5 ml) was collected from conjunctiva and the serum uric acid content was determined. On 30th day after treatment with antigout peptides, the rats were anaesthetized with 3% pentobarbitol sodium, and 5 ml of blood was collected from coeliac artery and the content of serum creatinine and urea nitrogen were determined at the same time in addition to the serum uric acid content.

Serum uric acid assay was carried out according to tungstic acid method, which was performed and determined strictly according to the instructions of the kit.

Serum urea nitrogen and creatinine assays: serum urea nitrogen content was determined according to diacetylmonoxime method; and the serum creatinine content was determined according to picric acid method. Specific operations were performed strictly according to the instructions of the kit.

Statistical processing: all the data were expressed in ($\bar{X}\pm s$) and processed with spss 16.0 statistical software. Comparisons among groups were performed with t-test method, and $p<0.05$ would indicate that the difference is statically significant.

TABLE 1

Effects of tuna extracts on the change of body weight of rats having hyperuricemia induced by potassium oxonate ($\bar{X} \pm s$)

| Groups | Before administration | | 10th day after treatment | | 20th day after treatment | | 30th day after treatment | |
| --- | --- | --- | --- | --- | --- | --- | --- | --- |
| | n | Body Weight (g) | n | Body Weight (g) | n | Body Weight (g) | n | Body Weight (g) |
| Normal Group | 15 | 197.2 ± 13.8 | 15 | 251.1 ± 14.1 | 15 | 289.7 ± 23.4 | 15 | 298.4 ± 26.0 |
| Model Group | 15 | 209.9 ± 14.8 | 15 | 246.5 ± 15.4 | 15 | 281.3 ± 21.1 | 15 | 307.3 ± 27.7 |
| Tuna extract 1 | 15 | 198.5 ± 9.5 | 15 | 242.1 ± 17.5 | 15 | 273.1 ± 25.7 | 15 | 285.7 ± 25.2 |
| Tuna extract 2 | 15 | 202.6 ± 9.3 | 15 | 244.8 ± 15.1 | 15 | 265.3 ± 19.5 | 15 | 288.5 ± 32.5 |
| Tuna extract 3 | 15 | 200.2 ± 10.9 | 15 | 248.9 ± 18.6 | 15 | 283.6 ± 27.0 | 15 | 294.7 ± 37.7 |
| Pacific saury extract | 15 | 199.7 ± 9.3 | 15 | 248.9 ± 14.2 | 15 | 278.1 ± 17.1 | 15 | 288.0 ± 27.0 |
| Golden thread extract | 15 | 198.5 ± 9.5 | 15 | 242.1 ± 17.5 | 15 | 273.1 ± 25.7 | 15 | 285.7 ± 25.2 |
| Spanish mackerel extract | 15 | 200.8 ± 8.0 | 15 | 239.2 ± 16.6 | 15 | 269.6 ± 28.2 | 15 | 281.2 ± 31.1 |
| Tuna extract control group A | 15 | 200.9 ± 9.5 | 15 | 243.1 ± 17.8 | 15 | 276.4 ± 29.6 | 15 | 278.3 ± 30.1 |
| Tuna extract control group B | 15 | 200.2 ± 10.9 | 15 | 248.9 ± 18.6 | 15 | 283.6 ± 27.0 | 15 | 294.7 ± 37.7 |

Notes:
as compared to normal control group: $^a p < 0.01$, $^c p < 0.01$;
as compared to model group: $^b p < 0.01$; $^e p < 0.05$, $^f p > 0.05$.

TABLE 2

Effects of different treatment duration of tuna extracts on serum uric acid content of rats having hyperuricemia induced by potassium oxonate ($\bar{X} \pm s$)

| Groups | Before administration | | 10th day after treatment | | 20th day after treatment | | 30th day after treatment | |
| --- | --- | --- | --- | --- | --- | --- | --- | --- |
| | n | Uric acid value (μmol/L) | n | Uric acid value (μmol/L) | n | Uric acid value (μmol/L) | n | Uric acid value (μmol/L) |
| Normal group | 15 | 74.1 ± 17.7 | 15 | 83.9 ± 15.2 | 15 | 75.7 ± 13.1 | 15 | 96.1 ± 10.9 |
| Model group | 15 | 326.3 ± 36.2 | 15 | 313.4 ± 55.7$^a$ | 15 | 319.8 ± 20.9$^a$ | 15 | 317.9 ± 54.9$^a$ |
| Tuna extract 1 | 15 | 294.3 ± 27.5 | 15 | 260.0 ± 54.8$^c$ | 15 | 2270.4 ± 40.9$^e$ | 15 | 272.2 ± 30.2$^b$ |
| Tuna extract 2 | 15 | 349.1 ± 84.0 | 15 | 341.3 ± 108.8$^f$ | 15 | 283.9 ± 33.6$^b$ | 15 | 258.6 ± 41.5$^b$ |
| Tuna extract 3 | 15 | 288.7 ± 34.7 | 15 | 327.0 ± 65.2$^f$ | 15 | 281.8 ± 23.3$^b$ | 15 | 257.1 ± 23.8$^b$ |
| Pacific saury extract | 15 | 329.2 ± 43.8 | 15 | 324.4 ± 66.6$^f$ | 15 | 308.4 ± 33.1$^g$ | 15 | 313.4 ± 20.4$^f$ |
| Golden thread extract | 15 | 294.3 ± 27.5 | 15 | 310.0 ± 54.8$^f$ | 15 | 313.4 ± 40.9$^f$ | 15 | 312.2 ± 30.2$^f$ |
| Spanish mackerel extract | 15 | 316.7 ± 39.8 | 15 | 350.4 ± 68.6$^f$ | 15 | 340.6 ± 47.3$^f$ | 15 | 347.8 ± 38.9$^f$ |

TABLE 2-continued

Effects of different treatment duration of tuna extracts on serum uric acid content of rats having hyperuricemia induced by potassium oxonate ($\overline{X} \pm s$)

| Groups | Before administration | | 10th day after treatment | | 20th day after treatment | | 30th day after treatment | |
|---|---|---|---|---|---|---|---|---|
| | n | Uric acid value (μmol/L) | n | Uric acid value (μmol/L) | n | Uric acid value (μmol/L) | n | Uric acid value (μmol/L) |
| Tuna extract control group A | 15 | 314.8 ± 30.2 | 15 | 322.2 ± 54.3$^f$ | 15 | 338.5 ± 38.8$^f$ | 15 | 318.4 ± 66.7$^f$ |
| Tuna extract control group B | 15 | 288.7 ± 34.7 | 15 | 327.0 ± 65.2$^f$ | 15 | 331.8 ± 23.3$^f$ | 15 | 357.1 ± 23.8$^f$ |

Notes:
as compared to normal control group: $^a$p < 0.01, $^c$p > 0.05;
as compared to model group: $^b$p < 0.01; $^e$p < 0.05, $^f$p > 0.05.

TABLE 3

Effects of administration of tuna extracts for 30 d on serum serum creatinine and urea nitrogen contents of rats having hyperuricemia induced by potassium oxonate ($\overline{x} \pm s$)

| Groups | Animal number | Creatinine (μmol/L) | Urea nitrogen (mmol/L) |
|---|---|---|---|
| Normal group | 15 | 33.3 ± 9.3 | 120.7 ± 29.7 |
| Model group | 15 | 59.8 ± 9.5$^a$ | 198.9 ± 52.5$^a$ |
| Allopurinol group | 15 | 52.9 ± 10.8$^b$ | 153.7 ± 29.7$^b$ |
| Tuna extract 1 | 15 | 44.5 ± 6.6$^b$ | 153.5 ± 34.0$^b$ |
| Tuna extract 2 | 15 | 49.8 ± 6.8$^b$ | 161.3 ± 49.1$^b$ |
| Tuna extract 3 | 15 | 56.5 ± 12.8$^b$ | 136.8 ± 28.6$^b$ |
| Pacific saury extract | 15 | 71.0 ± 16.9$^f$ | 189.3 ± 30.1$^a$ |
| Golden thread extract | 15 | 64.5 ± 6.6$^a$ | 193.5 ± 34.0$^a$ |
| Spanish mackerel extract | 15 | 62.6 ± 6.8$^a$ | 185.1 ± 25.9$^e$ |
| Tuna extract control group A | 15 | 71.5 ± 12.2$^f$ | 178.1 ± 63.8$^a$ |
| Tuna extract control group B | 15 | 76.5 ± 12.8$^f$ | 196.8 ± 28.6$^f$ |

Notes:
as compared to normal control group:
$^a$p < 0.01,
$^c$p > 0.05; as compared to model group:
$^b$p < 0.01;
$^e$p < 0.05,
$^f$p > 0.05.

Since rats share 90% genes with human beings, rats are globally recognized experimental model in the physiological and disease studies on human bodies. During the experiments for verification of uric acid-lowering effects, due to the presence of uricase in rat body, the uric acid will degrade during the metabolic process. Therefore, in the present animal experiment, rats were intragastricly administered with potassium oxonate everyday to block the effects of uricase in the rat body, such that the serum uric acid level of the rat would increase, and rats having a uric acid content of greater than 110 umol·L$^{-1}$ were determined to be successful models and were further used for the experiments by intragastric administration.

As is shown in Table 1, before and after the treatment of the model animals with tuna extracts and control samples, there is no significant difference in body weight amongst those groups of rats., indicating that the administration did not cause negative effects.

Potassium oxonate, which is an inhibitor of uricase, can act as a chemical inducer to inhibit the decomposition of uric acid, so as to increase the serum uric acid level in vivo, and thus create the animal model having hyperuricemia. As is shown in Table 2, the serum uric acid contents of rats in the model group and those groups before administration are significantly higher than that in normal control group (p<0.01) after they were treated with potassium oxonate for 1 week. On 10th, 20th and 30th days after treatment with potassium oxonate, the serum uric acid contents of rats in the model group were significantly higher than that in normal control group (p<0.01). For the model rats having hyperuricemia, after treatment with drugs, on the 10th day after administration with the tested drug tuna extract 1 and on the 20th day and 30th day after administration with the tested tuna extracts 2 and 3, the serum uric acid contents of rats in model group were significantly lowered (p<0.05, p<0.01), and the effects were stable. However, on the 30th day after treatment with Pacific saury extract, golden thread extract, Spanish mackerel extract, and tuna control groups A and B still did not show any uric acid-lowering effects (p>0.05). The group for allopurinol had a very significant effect in the reduction of the serum uric acid in rats in model group (p<0.01). As is shown in Table 2, the fish extracts obtained by the same process with different raw materials did not show the effect of lowering the serum uric acid in rats in model group, indicating that only the tuna contains certain active fragments with uric acid-lowering activity released after biological enzymolysis. In addition, tuna extracts (tuna extracts control 1 and 2) obtained by hydrolysis of tuna as raw material with enzyme formulation other than those used in the present invention did not have significant uric acid-lowering effects, thereby indicating that it is necessary for the tuna to be hydrolyzed by one or more ezymes of acid protease, papain, pepsin, trypsin, proteolytic enzyme, NEUTRASE® (Bacillus amyloliquefaciens protease), FLAVOURZYME® (Aspergillus oryzae protease) and ALCALASE® (Bacillus lichenformis protease), in order to release the fragments with uric acid-lowering activity contained therein. Therefore, tuna extracts prepared by the method of the present invention have better application prospect.

The peptide powder prepared by the method for the preparation of a protein peptide as provided in examples of the present invention is capable of chelating metal ions, while metal ions are activators for the catalytic reaction of xanthine oxidase which is the key enzyme in purine metabolism, and thus chelation of metal ions by peptides can inhibit the activity of xanthine oxidase, reducing the generation of uric acid, lowering the plasma uric acid level, and thereby effectively preventing and treating gout and hyperuricemia, and thus have a significant effect in improvement of gout syndrome.

In practical application, the peptide powder of interest of the present invention can be combined with Chinese herbal medicine such as Smilacis Glabrae Rhizoma, Cichorii Herba, Plantaginis Herba, Coicis Semen, Curcumae Longae Rhizoma, etc. to prepare a health care food product having uric acid-lowering function. It can also be prepared into food products with medicinal and edible materials such as Coicis Semen, Cheaenomelis Fructus, Dioscoreae Rhizoma, etc., vegetables containing potassium such as celery, etc., fresh ginger, and garlic.

The above description of the disclosed examples enables those skilled in the art to realize or carry out the present invention. Various changes to these examples will be obvious to those skilled in the art, and the general principle can be realized in other examples without departing from the spirits or scope of the present invention. Therefore, the present invention will not be limited to these examples illustrated herein, but will be in conformity with the broadest scope in consistent with the principle and novel features disclosed herein.

The invention claimed is:

1. A method for the preparation of a protein peptide comprising the steps:
   (1) mincing tuna from which head and viscera has previously been removed, heating after adding water or heating with water steam to obtain pretreated tuna;
   (2) enzymolysing the pretreated tuna, deactivating the enzyme, centrifuging to obtain a supernatant;
   (3) concentrating the supernatant and drying to obtain the peptide powder of interest, which is the protein peptide, wherein the protease used in enzymolysis is one or more of acid protease and NEUTRASE® (neutral, zinc metallo endo-protease from *Bacillus amyloliquefaciens*), and the total amount of proteases used is 0.2% to 3.2% by weight of the pretreated tuna.

2. The method according to claim 1, wherein the step of heating after adding water or heating with steam comprises heating at 80 to 100° C. for 5 to 30 min with steam or water.

3. The method according to claim 1, wherein the steps of enzymolysis and deactivating the enzyme comprise: mixing the pretreated tuna with protease at a temperature of 50 to 60° C. for 3.0 to 9.0 h; deactivating the enzyme at a temperature of 90 to 100° C. for 10 to 30 min after completion of the reaction.

4. The method according to claim 1, further comprising removing impurities in the supernatant to obtain a treated supernatant before concentration.

5. The method according to claim 4, wherein the step of removing impurities in the supernatant comprises:
   (1) adding activated charcoal to the supernatant in an amount of 0.3% to 2.5% by weight of the supernatant;
   (2) stirring at 50 to 90° C. for 0.5 to 2.0 h;
   (3) removing the activated charcoal by filtration.

6. The method according to claim 1, wherein the step of concentration is conducted to achieve a solids of 30% to 45% by weight with a three-effect concentrator under a vacuum condition of 0.03 to 0.08 MPa at 60 to 80° C.

7. The method according to claim 1, wherein the tuna is one or more of skipjack tuna, bluefin tuna, albacore tuna, and yellowfin tuna.

* * * * *

UNITED STATES PATENT AND TRADEMARK OFFICE
CERTIFICATE OF CORRECTION

PATENT NO. : 10,455,849 B2
APPLICATION NO. : 15/140925
DATED : October 29, 2019
INVENTOR(S) : Xiaolei Guo et al.

Page 1 of 1

It is certified that error appears in the above-identified patent and that said Letters Patent is hereby corrected as shown below:

On the Title Page

Item (71) Applicant, delete the entirety of the item and replace with --INFINITUS (CHINA) COMPANY LTD., Jiang Men City (CN)-- therefor.

Item (72) Inventors, delete the entirety of the items and replace with --Xiaolei GUO, Jiang Men City (CN); Chung Wah MA, Jiang Men City (CN); Bin SHI, Jiang Men City (CN); Ming LIANG, Jiang Men City (CN); Ting ZHANG, Jiang Men City (CN)-- therefor.

Item (73) Assignee, delete the entirety of the item and replace with --INFINITUS (CHINA) COMPANY LTD., Jiang Men City, (CN)-- therefor.

Item (57) Abstract, Line 8, delete "enzymolyzing" and insert --enzymolysing-- therefor.

Signed and Sealed this
Tenth Day of December, 2019

Andrei Iancu
*Director of the United States Patent and Trademark Office*